United States Patent [19]

Lubowe

[11] Patent Number: 4,474,763

[45] Date of Patent: Oct. 2, 1984

[54] SKIN PREPARATION

[76] Inventor: Irwin I. Lubowe, 45 Sutton Place South, New York, N.Y. 10022

[21] Appl. No.: 395,990

[22] Filed: Jul. 7, 1982

[51] Int. Cl.³ ...................... A61K 37/02; A61K 31/56
[52] U.S. Cl. ..................................... 424/177; 424/359; 424/238
[58] Field of Search ......................... 424/238, 359, 177

[56] References Cited

U.S. PATENT DOCUMENTS

| 3,364,118 | 1/1968 | Howard et al. | 424/177 |
| 3,991,184 | 11/1976 | Kludas et al. | 424/177 |
| 4,080,309 | 9/1977 | Chen et al. | 424/70 |
| 4,080,310 | 9/1977 | Chen et al. | 424/70 |
| 4,327,078 | 4/1982 | Charlet et al. | 424/177 |

FOREIGN PATENT DOCUMENTS 2405069  5/1979  France .

Primary Examiner—Delbert R. Phillips
Assistant Examiner—F. T. Moezie
Attorney, Agent, or Firm—N. J. Aquilino

[57] ABSTRACT

A composition useful for smoothing the skin, reducing wrinkles, and improving the moisture level and tone of the skin having minor proportions of the pharmocologically active agents pregnenolone and elastin in a pharmaceutically acceptable hydrophillic carrier vehicle. The composition may further include substances selected from aloe vera, tocopherols, vegetable, animal and synthetic oils and waxes, allantoin, and skin penetration enhancing agents, such as the lower alkyl sulfoxides.

10 Claims, No Drawings

SKIN PREPARATION

BACKGROUND OF THE INVENTION

This invention relates to compositions for topical application to human animal tissue and more specifically to a synergistic combination of pharmocologically active agents comprising pregnenolone or a pharmaceutically acceptable salt thereof and an elastin or an elastin hydrozylate in a pharmaceutically acceptable carrier vehicle for the purpose of improving the condition of the skin. Lines and wrinkles of the facial skin are primarily a natural result of the ageing process, but contributory factors include exposure to the sun or the resulting ultraviolet radiation, faulty care, stress, nutritional deficiencies and genetic propensity.

Numerous topical treatments are known in the art for mitigating this condition. The known compositional methods of treatment may conveniently be classified as either cosmetically based or active agent based.

Cosmetically based approaches have as their aim the masking, filling, or offsetting through shadowing and similar artistic techniques of unsightly facial lines and wrinkles. The resultant compositions are employed for their coloring, shading, and levelling or filling effect on the skin.

In the physiologically active agent approach, with which the invention is concerned, a composition is directed to effecting at the least a temporary physiological improvement in the condition of the skin without resorting to masking, filling and artistry. Most desirably, these latter compositions contribute toward the lasting improvement and enhancement of the quality of the skin, particularly with respect to diminishing lines and wrinkles around the eyes, in the smaller area of the cheeks and around the upper and lower lips.

Pharmacologically active agents directed to the instant problem known in the art include the use, either singly or in combination, of skin proteins such as elastin and collagen. Exemplary of these teachings are U.S. Pat. Nos. 3,991,184; 4,179,333; 3,941,722; and German Pat. No. 2,804,024.

The utilization of steroids and steroid-like substances for diminishing lines and wrinkles is taught in U.S. Pat. No. 2,791,534 and in British Pat. No. 768,129.

The combination of a skin protein with a steroid is taught in Chemical Abstracts, Vol. 80: 195942 which discloses a skin substance such as collagen with testosterone which is a potent androgen.

Pages 105-7, THE SCIENCE AND TECHNOLOGY OF COSMETICS (1980), edited by Sagarin, presents a discussion of pregnenolone in relation to the skin ageing process. Reference is made to combinations of estrogenic substances with surfactants, natural hydrocolloids and other undefined natural products.

Other patents of general interest are U.S. Pat. Nos. 3,627,871; 4,131,650; and 4,046,886.

None of the prior art references suggest or teach the specific combinations of elastin and pregnenolone used together as a topical skin applicant.

SUMMARY OF THE INVENTION

The present invention combines elastin and pregnenolone or a pharmaceutically acceptable salt thereof with other ingredients to provide a skin applicant which in specified proportions has a synergistic effect in acting to diminish the appearance of lines and wrinkles of the face.

In single blind tests conducted by the inventor in over 200 patients afflicted with noticeable and displeasing lines and wrinkles, positive improvements were reported by the overwhelming majority of patients who daily applied a composition made in accordance with the teachings of the present invention. These improvements contrasted sharply and unmistakably with the comparatively modest improvements realized from the use, singly, of either pregnenolone or elastin in identical pharmaceutical carrier vehicles. These results are all the more surprising when it is recognized that the amount of pregnenolone in a preferred embodiment of the formulation, namely 0.025%, is substantially lower than recommended effective levels previously disclosed in the art. This development takes on greater importance in view of the medical desirability of minimizing systemic absorption of potent steroid and steroid-like substances.

While the instant composition may be applied once daily with salutory effect, it has been found that two separate applications at least six hours apart, preferably one in the morning and one before retiring, brings optimal results.

Further, while not altering the concentrations of either the elastin or the pregnenolone, it appears that varying the formulation of the carrier vehicle in the morning and evening compositions is advantageous.

The morning preparation is a thin oil in water emulsion which is rapidly absorbed into the skin after which a foundation lotion and make-up is applied.

The evening or night preparation preferably incorporates a more viscous hydrophillic ointment carrier vehicle.

The principal pharmacollogically active ingredients of the invention include pregnenolone or a salt thereof, such as pregnenolone acetate at weight concentrations of from about 0.001% to about 1.0%, and most preferably at a concentration of about 0.025%, and water-soluble elastin at weight concentrations of from about 0.5% to about 5.0%, and most preferably at a concentration of about 1.0%.

Pregnenolone acetate is the preferred form of pregnenolone primarily due to its desirable solubility characteristics and commercial availability; however, it will be appreciated that pregnenolone, pregnenolone succinate, pregnenolone methyl ether and analogs possessing similar pharmacological properties may be substituted for pregnenolone acetate or used in combination therewith. It will be further understood that due to differences in the solubility characteristics between the different forms of pregnenolone, changes in the carrier vehicle composition may be required.

The protein, elastin, as used in this invention, is understood to be the water or organic solvent soluble form of elastin made from the load bearing fibers of animal connective tissue. Solubilizing elastin typically requires some rupturing of the peptide bonds and the forms preferred for use in this invention are water-soluble elastin hydrolyzates. These products and the preparation thereof are described, for example, in German Pat. Nos. 2,656,226; 2,705,670; and U.S. Pat. No. 4,179,333, all of which are incorporated herein by way of reference. As described in U.S. Pat. No. 4,179,333, a suitable water-soluble elastin hydrolyzate for use herein may be prepared from starting materials containing elastin, such as hide wastes and tendons. The elastin hydrolyzate may be prepared, for example, from the neck ligaments (ligamentum nuchae) of slaughtered livestock, such as cattle or pigs by first subjecting the starting material to acid treatment at a pH below about 4 and at an elevated temperature, and then enzymatically degrading the acid-treated material, while in communited form, in an aqueous both in the presence of urea, with an alkaline proteinase having an activity optimum in a range between pH 9 and pH 13, the initial pH of the enzymatic treatment being within the pH range optimum for the enzyme employed. After the degradation is completed, the hydrolyzate solution is treated for a short time at temperatures of about 90 degrees C., whereby any still-active enzyme is inactivated. The mixture may then be purified by filtration and reduced to the desired concentration or dried, for example, by conventional spray drying, to a powder. The resultant elastin product, in its final purified form, is a substantially clear, non-odorous substance.

With respect to the terms "pharmaceutically acceptable carrier vehicle" and "carrier vehicle" as used therein, is meant any liquid, gel, emulsion cream, ointment, fluid ointment base, solvent, diluent and the like, which is suitable for use in contact with living animal tissue including living human tissues without any untoward physiological response and which desirably is capable of co-dissolving the pharmocologically active agents and which further will not interact with the other components of the composition in a deleterious manner and which still further can be used to establish the compositions herein in their preferred forms.

The following examples are intended to illustrate typical compositions of this invention but are not intended to be limiting thereof.

EXAMPLE I

| INGREDIENT | PERCENTAGE (By Weight) |
| --- | --- |
| Pregnenolone Acetate | 0.025 |
| Elastin | 1.000 |
| Methyl Paraben | .025 |
| Propyl Paraben | .015 |
| Sodium Lauryl Sulfate | 1.0 |
| Propylene Glycol | 12.0 |
| Stearyl Alcohol | 25.0 |
| White Petrolatum | 25.0 |
| Polyoxyl 40 Stearate | 5.0 |
| Isopropyl Myristate | 0.025 |
| Purified Water | Balance |

The pregnenolone and elastin are combined with the other ingredients, which form a hydrophilic pharaceutically acceptable carrier vehicle, are blended mechanically to provide a water-removable ointment. In accordance with the teachings of the invention, this preparation is preferably applied to affected skin in the evening or at night before retiring.

EXAMPLE II

| INGREDIENT | PERCENTAGE (By Weight) |
| --- | --- |
| Pregnenolone Acetate | 0.025 |
| Elastin | 1.0 |
| Mineral Oil | 6.0 |
| Magnesium Aluminum Silicate | 1.0 |
| Laneth-10 Acetate (veegum) | 2.0 |
| Cetyl Alcohol | 3.0 |
| Isopropyl Palmitate | 1.0 |
| Pluronic L-122 Polyol | 4.0 |
| Perservative (BHT or BHA) | 1.0 |

EXAMPLE II-continued

| INGREDIENT | PERCENTAGE (By Weight) |
| --- | --- |
| Purified Water | Balance |

The above ingredients are mechanically blended and provide a thin oil in water emulsion to be applied, in accordance with the teachings of the invention, in the morning before application of the foundation and make-up.

EXAMPLE III

| INGREDIENT | PERCENTAGE (By Weight) |
| --- | --- |
| Pregnenolone Acetate | 0.025 |
| Elastin | 1.0 |
| Cholesterol | 3.0 |
| Stearyl Alcohol | 3.0 |
| White Wax | 8.0 |
| White Petrolatum | Balance |

The above ingredients are prepared by mechanical blending with the resultant product forming a protective and water absorbable ointment possession excellent absorption properties.

EXAMPLE IV

| INGREDIENT | PERCENTAGE (By Weight) |
| --- | --- |
| Pregnenolone Acetate | 0.025 |
| Elastin | 1.0 |
| Hydrophilic Ointment USP | Balance |

The above ingredients are prepared by mechanically blending to form the skin preparation.

The above described compositions may also include a number of adjunct substances which further increase the efficacy of the instant invention and/or its aesthetic appeal.

For example, collagen, another skin protein which like elastin is depleted in ageing skin, may be added to any of the foregoing examples in a concentration preferably between about 0.5% and 10%, and most preferably in a concentration of about 1.0%.

Further, such well known and established cosmetic ingredients as aloe vera, aloe-emodin, and allantoin may be present in the instant preparation at concentration of up to about 50%.

Vitamins selected from the water soluble B group and oil soluble A, D and E groups may also be added. Vitamin E, present as mixed stereo-isomers, including the alpha stereo isomer, is particularly advantageous.

The addition of a sunscreen is further contemplated, particularly in the morning-applied preparation of Example II. The sunscreen not only serves to protect the skin from the deleterious effects of ultraviolet radiation, but adds a measure of protection to the components of the subject preparations which are effected by ultraviolet radiation. Preferred sunscreens, desirably present in the formulation at concentrations from about 0.5% to about 10%, are selected from the group consisting of p-aminobenzoic acid, homomenthyl salicylate, isopropyl cinnamate, p-methoxycinnamic acid, 2-ethylhexyl salicylate, dipropyleneglycol salicylate, monoglyceral p-aminobenzoate, digalloyltrioleate and menthyl anthranilate.

Since an effective carrier vehicle must necessarily exhibit excellent tissue penetration characteristics, any of the foregoing examples may contain compatible surface active agents. These agents are well known in the cosmetic art and are discussed, for example, in *Remington's Pharmaceutical Science, McCutcheon's Detergents,* and *Sagarin's Science and Technology of Cosmetics,* all of which are incorporated herein by way of reference.

Still greater tissue penetration of active agents can be achieved through incorporation of the newer enhanced penetrating agents. The most widely known such agent is dimethyl sulfoxide and homologous low molecular weight alkyl sulfoxides. For maximum effect, these sulfoxides generally require concentration levels in the carrier vehicle of at least 30% by weight, and more preferably 60–75%. Other suitable penetrating agents include phosphine oxides, sucrose monooleates, methyl acetamide and combinations thereof. Full discussions of these enhanced penetration agents and their utilization in topical preparations are found in U.S. Pat. Nos. 4,046,886; 3,326,768; 3,527,864; and 3,551,554, all of which are incorporated herein by way of reference.

Of course, the preparations incorporating the active agents of the present invention may contain the normal processing aids, such as dispersing and rheological agents, as well as fragrances, coloring agents, film forming agents, rubefactants, and compatible preservative agents, or any combination thereof.

I claim:

1. A pharmaceutical preparation of for topical administration consisting essentially of an intimate mixture of pregnenolone or a pharmaceutically acceptable salt thereof and a water soluble elastin with a pharmaceutically acceptable carrier, said pregnenolone or salt thereof being present at concentration between about 0.001% to about 1.0% by weight, and said water soluble elastin being present at concentrations between about 0.5% and about 10% by weight.

2. The pharmaceutical preparation of claim 1 comprising a pregnenolone salt selected from the group consisting of pregnenolone acetate, pregnenolone succinate and pregnenolone methyl ether.

3. The pharmaceutical preparation of claim 1 wherein said pharmaceutically acceptable carrier is in the form selected from the group consisting of creams, gels, ointments, salves, liquids, and emulsions.

4. The pharmaceutical preparation of claim 1 additionally comprising at least one adjunct selected from the group consisting of collagen, aloe vera, oils, waxes, allantoin, vitamins, sunscreens, rebefactants, surfactants, tissue penetration enhancing agents, fragrance and coloring agents.

5. A pharmaceutical preparation for topical administration consisting essentially of by weight:
   about 0.025% pregnenolone acetate:
   about 1.0% elastin hydrolyzate; and
   about 98.975% hydrophilic pharmaceutically acceptable carrier vehicle.

6. A method for diminishing lines and wrinkles of living human tissue comprising: applying to substantially clean human skin a pharmaceutical preparation consisting essentially of between about 0.001% to about 1.0% by weight pregnenolone acetate, between about 0.5% to about 5% by weight elastin hydrolyzate, and the balance pharmaceutically acceptable carrier.

7. The method of claim 6 wherein said application is repeated at least twice daily at intervals of at least six hours.

8. The method of claim 7 wherein a first application is applied upon waking and second application is applied before retiring.

9. The method of claim 6, consisting essentially of about 0.025% pregnenolone acetate, about 1.0% elastin hydrolyzate, and the balance a pharmaceutically acceptable carrier.

10. The pharmaceutical preparation of claim 5 consisting essentially of about 0.025% pregnenolone acetate, about 1.0% elastin hydrolyzate, and the balance a hydrophilic pharmaceutically acceptable carrier.

* * * * *